United States Patent [19]

Thompson

[11] Patent Number: 5,145,664
[45] Date of Patent: Sep. 8, 1992

[54] MOUTHWASH

[75] Inventor: William J. Thompson, Ancaster, Canada

[73] Assignee: Thompson McKay Pharmaceuticals, Ltd., Ancaster, Canada

[21] Appl. No.: 720,669

[22] Filed: Jun. 25, 1991

[30] Foreign Application Priority Data

Jun. 25, 1990 [CA] Canada .................. 2019719

[51] Int. Cl.$^5$ .................. A61K 7/16; A61K 7/22
[52] U.S. Cl. .................. 424/49; 424/54
[58] Field of Search .................. 424/49-58

[56] References Cited

U.S. PATENT DOCUMENTS

| | | | |
|---|---|---|---|
| 3,689,636 | 9/1972 | Svajda | 424/49 |
| 4,024,237 | 5/1977 | Eichel et al. | 424/49 |
| 4,132,770 | 1/1979 | Barth | 424/49 |
| 4,370,314 | 1/1983 | Gaffar | 424/54 |
| 4,618,489 | 10/1986 | Pollock et al. | 424/49 |
| 4,631,185 | 12/1986 | Kim | 424/49 |
| 4,657,758 | 4/1987 | Goldemberg et al. | 424/49 |
| 4,666,708 | 5/1987 | Goldemburg et al. | 424/49 |
| 4,861,582 | 8/1989 | Pollock et al. | 424/49 |
| 4,919,918 | 4/1990 | Cole et al. | 424/49 |
| 4,925,655 | 5/1990 | Smiger et al. | 424/53 |
| 4,971,782 | 11/1990 | Rudy et al. | 424/53 |
| 4,971,785 | 11/1990 | Wilson et al. | 424/49 |

FOREIGN PATENT DOCUMENTS 1469398  4/1977  United Kingdom .

Primary Examiner—Shep K. Rose
Attorney, Agent, or Firm—Hoffman, Wasson & Gitler

[57] ABSTRACT

There is described an improved alcohol free mouthwash comprising sodium chloride, sodium bicarbonate and water.

10 Claims, No Drawings

MOUTHWASH

The present invention relates to the field of oral hygienics. In particular, the present invention provides a novel mouthwash formulation.

Mouthwashes and oral rinses have been in use for many years. They are utilized by hospitals and other health care facilities and dentists, and in general by consumers. Most, if not all, commercially available mouthwashes contain a fairly high percentage—up to thirty percent being typical—of ethyl alcohol. While these alcohol-containing mouthwashes are generally safe and effective, there are several important reasons why an alcohol-free mouthwash is desirable. The reasons include:

i) High alcohol mouthwashes have been linked in some cases to increased incidence of mouth and throat cancer;

ii) a large number of persons cannot tolerate alcohol and must, for health reasons, avoid its use;

iii) alcohol-containing mouthwashes can be a poison hazard to a small child;

iv) alcohol-containing mouthwashes are often abused by alcoholics;

v) alcohol-containing mouthwashes must be avoided by some persons because of religious convictions;

vi) alcohol in a mouthwash may irritate the protective layers of the mouth and throat, or dry out inflamed tissues.

In view of the foregoing, an object of the present invention is to provide a safe and effective mouthwash that does not utilize alcohol in any form.

In a broad aspect, the present invention relates to an alcohol free mouthwash comprising: (i) sodium chloride; (ii) sodium bicarbonate; a flavoring agent and as a solubilizing agent therefore, polysorbate 20, being a mixture of partial lauric esters of sorbitol and its mono- and di-anhydrides copolymerized with approximately 20 mols of ethylene oxide for each mol of sorbitol and its anhydrides; and water, said sodium chloride and sodium bicarbonate being dissolved in said water and present in a suitable quantity to produce a solution substantially isotonic with human oral mucosa.

In another broad aspect, the present invention relates to a mouthwash, containing in an 8500 liter solution; 23 35 25% Kg NaCl; 15±25% Kg Na HCO$_{HCO3}$; 10.6 liters ±20% oil of peppermint; 60 liters ±20% Tween 20, which is a trademark for polysorbate 20, being a mixture of partial lauric esters of sorbitol and its mono- and di-anhydrides copolymerized with approximately 20 mols of ethylene oxide for each mold of sorbitol and its anhydrides. 5 Kg ±10% sodium saccharin; 1.19 Kg ±10% propyl paraben; 10.0 Kg ±10% methyl paraben; and water, The compound polysorbate 20 is also referred to herein as Tween 20. Tween 20 is available from Atlas Chemical Company and other suppliers. It is a clear or slightly opalescent yellow or brownish yellow oily liquid with a faint characteristic odor. Its relative density is 1.1, its viscosity at 25° C. is about 400 CP.

The present invention utilizes, as active agents, sodium chloride and sodium bicarbonate. In combination with the balance of the mouthwash formulation, sodium chloride and sodium bicarbonate in relative quantities discussed below, produce a solution that is isotonic and thereby non-irritating to the oral mucosa. The sodium chloride and sodium bicarbonate act to maintain and restore the integrity of the tissues of the mouth and throat.

As a flavouring agent, the present invention utilizes oil of peppermint, solubilized with polysorbate 20. The use of this solubilizer is required in that alcohol, which is usually utilized to solubilize flavouring agents, is not present in the formulation of the present invention.

Manufacture of the present invention is illustrated in the following example:

EXAMPLE I

List of Materials

| | |
|---|---|
| Sodium Chloride USP | 22.66 Kg |
| Sodium Bicarbonate USP | 15.0 Kg |
| Oil of Peppermint | 10.63 Kg |
| Polysorbate 20 | 60 liters |
| Sodium Saccharin | 5 Kg |
| Propyl Paraben (a preservative) USP | 1.19 Kg |
| Methyl Paraben (a preservative) USP | 10.0 Kg |
| Benzalkonium chloride (antibacterial) | .85 Kg |
| Water | 8500 liters |

10.63 liters Oil of Peppermint is dissolved with 60 liters of Tween 20 in 100 liters of deionized water, to obtain solution "A".

22.66 Kg NaCl and 15 Kg NaHCO$_3$ are dissolved in 850 liters deionized water. To this is added solution "A", to obtain solution "B". 1.19 Kg Propyl Paraben, and 10.0 Kg Methyl Paraben are mixed with 7300 liters dionized water, and heated moderately, as required, to obtain solution, which is then cooled to ambient temperature. 5.0 Kg sodium saccharin, 0.85 Kg Benzalkonium Chloride, and colouring as desired are added, to obtain solution "C".

Solutions "B" and "C" are combined, and water is added to obtain 8500 liters of solution, which is then filtered to obtain a final product.

It will be noted that the above stated relative proportions of constituent elements of the formulation of the present invention may be varied up to ±25%.

The mouthwash product produced according to the foregoing procedure has been found to be an effective treatment of mouth sores and sore throat, as well as halitosis and dry mouth.

It is to be understood that the examples described above are not meant to limit the scope of the present invention. It is expected that numerous variants will be obvious to the person skilled in the field of pharmacological treatment of the mouth and throat, without any departure from the spirit of the invention. The appended claims, properly construed, form the only limitation upon the scope of the present invention.

I claim:

1. An alcohol free mouthwash consisting essentially of:

i) sodium chloride:

ii) sodium bicarbonate;

iii) a flavoring agent and as a solubilizing agent herefor, polysorbate 20, being a mixture of partial lauric esters of sorbitol and its mono- and di-anhydrides copolymerized with approximately 20 mols of ethylene oxide for each mol of sorbitol and its anhydrides; and iv) water, said sodium chloride and sodium bicarbonate being dissolved in said water and present in a suitable quantity to produce a solution substantially isotonic with human oral mucosa.

2. A mouthwash as described in claim 1, wherein said sodium chloride is present in an amount equal to 22.66 Kg ±25% (dry weight) per 8500 liters of mouthwash.

3. A mouthwash as described in claim 3, wherein said sodium bicarbonate is present in an amount equal to 15 Kg ±25% (dry weight) per 8500 liters of mouthwash.

4. A mouthwash as described in claim 1, further including a sweetening agent.

5. A mouthwash as described in claim 4, where said sweetening agent is sodium saccharin.

6. A mouthwash as described in claim 5, further including a preserving agent.

7. A mouthwash as described in claim 6, wherein said preserving agent is a mixture of propyl and methyl paraben.

8. A mouthwash as claimed in claim 3, further including, per 8500 liters:
   1.6 liters ±20% oil of peppermint
   60 liters ±20% polysorbate 20
   5.0 Kg ±10% sodium saccharin
   1.19 Kg ±10% propyl paraben
   1.0 Kg ±10% methyl paraben.

9. A mouthwash, as described in claim 8, further including an antibacterial agent.

10. A mouthwash, as described in claim 9, wherein said antibacterial agent is 0.85 Kg ±20% benzalkonium chloride.